US012788405B2

(12) United States Patent
Rashidi et al.

(10) Patent No.: US 12,788,405 B2
(45) Date of Patent: *Nov. 10, 2026

(54) DEVICES, SYSTEMS, AND METHODS FOR TREATING ANEURYSMS

(71) Applicant: Covidien LP, Mansfield, MA (US)

(72) Inventors: Mehdi Matteo Rashidi, Irvine, CA (US); Junwei Li, Irvine, CA (US); Belinko K. Matsuura, Encinitas, CA (US); David G. Matsuura, Solana Beach, CA (US); Nelson M. Siu, Encinatas, CA (US)

(73) Assignee: Covidien LP, Mansfield, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 18/791,050

(22) Filed: Jul. 31, 2024

(65) Prior Publication Data

US 2024/0390010 A1 Nov. 28, 2024

Related U.S. Application Data

(63) Continuation of application No. 17/816,398, filed on Jul. 30, 2022, now Pat. No. 12,070,221.

(51) Int. Cl.
*A61B 17/12* (2006.01)

(52) U.S. Cl.
CPC .... *A61B 17/12113* (2013.01); *A61B 17/1214* (2013.01); *A61B 2017/12054* (2013.01)

(58) Field of Classification Search
CPC .......... A61B 17/12113; A61B 17/1214; A61B 17/12172; A61B 17/12186;
(Continued)

(56) References Cited

U.S. PATENT DOCUMENTS

| | | | |
|---|---|---|---|
| 5,749,894 | A | 5/1998 | Engelson |
| 5,800,455 | A | 9/1998 | Palermo et al. |

(Continued)

FOREIGN PATENT DOCUMENTS

| | | | |
|---|---|---|---|
| EP | 2265193 | B1 | 11/2011 |
| EP | 3403597 | A1 | 11/2018 |

(Continued)

OTHER PUBLICATIONS

International Search Report and Written Opinion mailed Oct. 2, 2023, International Application No. PCT/IB2023/057193, 14 pages.

(Continued)

*Primary Examiner* — Tan-Uyen T Ho
*Assistant Examiner* — Osama Nemer
(74) *Attorney, Agent, or Firm* — Fortem IP LLP

(57) ABSTRACT

Devices, systems, and methods for treating aneurysms are disclosed herein. According to some embodiments, the present technology includes a treatment system comprising a delivery shaft, a manipulation shaft slidably positioned within the lumen of the delivery shaft, and an occlusive device configured for implantation within the aneurysm. The occlusive device can comprise a plurality of filaments that are secured to one another at a proximal end of the occlusive device by a cured material. The occlusive device can comprise inner and outer layers of braided filaments, wherein the proximal end region of the inner layer has an exposed portion that extends proximally beyond the proximal end region of the outer layer, and wherein the cured material extends into and fills interstices between the braided filaments at the proximal end regions of the inner and outer layers.

17 Claims, 10 Drawing Sheets

(58) Field of Classification Search
CPC .... A61B 17/12163; A61B 2017/12054; A61B 2017/00526; A61B 2017/12063
See application file for complete search history.

(56) References Cited

U.S. PATENT DOCUMENTS

| | | | | |
|---|---|---|---|---|
| 6,280,423 | B1 * | 8/2001 | Davey | A61M 1/30 604/525 |
| 10,398,441 | B2 | 9/2019 | Warner et al. | |
| 11,583,288 | B2 | 2/2023 | Gorochow | |
| 11,678,888 | B2 | 6/2023 | Shimizu et al. | |
| 11,826,863 | B2 * | 11/2023 | Li | A61B 17/12031 |
| 12,070,221 | B2 * | 8/2024 | Rashidi | A61B 17/12172 |
| 12,251,110 | B2 * | 3/2025 | Nguyen | A61B 17/12031 |
| 12,539,122 | B2 * | 2/2026 | Rashidi | A61B 17/12113 |
| 2003/0097149 | A1 * | 5/2003 | Edwards | A61B 17/00491 606/214 |
| 2003/0171739 | A1 | 9/2003 | Murphy et al. | |
| 2004/0097988 | A1 | 5/2004 | Gittings et al. | |
| 2006/0009799 | A1 | 1/2006 | Kleshinski et al. | |
| 2006/0116711 | A1 * | 6/2006 | Elliott | A61B 17/12022 606/200 |
| 2006/0247572 | A1 | 11/2006 | McCartney | |
| 2007/0265656 | A1 * | 11/2007 | Amplatz | A61B 17/12122 606/200 |
| 2011/0319926 | A1 * | 12/2011 | Becking | A61B 17/12022 606/200 |
| 2012/0071964 | A1 | 3/2012 | Cattaneo et al. | |
| 2013/0211492 | A1 | 8/2013 | Schneider et al. | |
| 2013/0261656 | A1 * | 10/2013 | Lorenzo | A61B 17/12154 606/200 |
| 2013/0261657 | A1 * | 10/2013 | Lorenzo | A61B 17/12113 606/200 |
| 2015/0313605 | A1 | 11/2015 | Griffin | |
| 2016/0008003 | A1 | 1/2016 | Kleshinski et al. | |
| 2016/0128699 | A1 | 5/2016 | Hadley et al. | |
| 2016/0206452 | A1 | 7/2016 | Berez et al. | |
| 2016/0249934 | A1 | 9/2016 | Hewitt et al. | |
| 2017/0224350 | A1 | 8/2017 | Shimizu et al. | |
| 2017/0367707 | A1 | 12/2017 | Divino | |
| 2019/0223881 | A1 | 7/2019 | Hewitt et al. | |
| 2020/0054344 | A1 | 2/2020 | Connor | |
| 2020/0367902 | A1 | 11/2020 | Cibulski et al. | |
| 2021/0128160 | A1 | 5/2021 | Li et al. | |
| 2021/0128165 | A1 | 5/2021 | Pulugurtha et al. | |
| 2021/0128168 | A1 | 5/2021 | Nguyen et al. | |
| 2021/0128169 | A1 | 5/2021 | Li et al. | |
| 2024/0032932 | A1 | 2/2024 | Rashidi et al. | |
| 2024/0032933 | A1 | 2/2024 | Rashidi et al. | |

FOREIGN PATENT DOCUMENTS

| | | | |
|---|---|---|---|
| WO | 2009132045 | A2 | 10/2009 |
| WO | 2015171268 | A2 | 11/2015 |
| WO | 2017106265 | A1 | 6/2017 |
| WO | 2022149141 | A1 | 7/2022 |
| WO | 2024026352 | A1 | 2/2024 |

OTHER PUBLICATIONS

International Search Report and Written Opinion mailed Nov. 14, 2023, International Application No. PCT/US2023/071026, 12 pages.

* cited by examiner

DEVICES, SYSTEMS, AND METHODS FOR TREATING ANEURYSMS

CROSS-REFERENCE TO RELATED APPLICATION(S)

The present application claims the benefit of priority to U.S. patent application Ser. No. 17/816,398, filed Jul. 30, 2022, which is incorporated by reference herein in its entirety.

TECHNICAL FIELD

The present technology generally relates to medical devices, and in particular to implantable devices for treating vascular defects.

BACKGROUND

An intracranial aneurysm is a portion of an intracranial blood vessel that bulges outward from the blood vessel's main channel. This condition often occurs at a portion of a blood vessel that is abnormally weak because of a congenital anomaly, trauma, high blood pressure, or for another reason. Once an intracranial aneurysm forms, there is a significant risk that the aneurysm will eventually rupture and cause a medical emergency with a high risk of mortality due to hemorrhaging. When an unruptured intracranial aneurysm is detected or when a patient survives an initial rupture of an intracranial aneurysm, vascular surgery is often indicated. One conventional type of vascular surgery for treating an intracranial aneurysm includes using a microcatheter to dispose a platinum coil within an interior volume of the aneurysm. Over time, the presence of the coil should induce formation of a thrombus. Ideally, the aneurysm's neck closes at the site of the thrombus and is replaced with new endothelial tissue. Blood then bypasses the aneurysm, thereby reducing the risk of aneurysm rupture (or re-rupture) and associated hemorrhaging. Unfortunately, long-term recanalization (i.e., restoration of blood flow to the interior volume of the aneurysm) after this type of vascular surgery occurs in a number of cases, especially for intracranial aneurysms with relatively wide necks and/or relatively large interior volumes.

Another conventional type of vascular surgery for treating an intracranial aneurysm includes deploying a flow diverter within the associated intracranial blood vessel. The flow diverter is often a mesh tube that causes blood to preferentially flow along a main channel of the blood vessel while blood within the aneurysm stagnates. The stagnant blood within the aneurysm should eventually form a thrombus that leads to closure of the aneurysm's neck and to growth of new endothelial tissue, as with the platinum coil treatment. One significant drawback of flow diverters is that it may take weeks or months to form aneurysmal thrombus and significantly longer for the aneurysm neck to be covered with endothelial cells for full effect. This delay may be unacceptable when risk of aneurysm rupture (or re-rupture) is high. Moreover, flow diverters typically require antiplatelet therapy to prevent a thrombus from forming within the main channel of the blood vessel at the site of the flow diverter. Antiplatelet therapy may be contraindicated shortly after an initial aneurysm rupture has occurred because risk of re-rupture at this time is high and antiplatelet therapy tends to exacerbate intracranial hemorrhaging if re-rupture occurs. For these and other reasons, there is a need for innovation in the treatment of intracranial aneurysms.

SUMMARY

The present technology is directed to occlusive devices for treating aneurysms and associated systems and methods. Some embodiments include an occlusive device comprising a plurality of braided filaments that are secured to one another at a proximal end of the occlusive device via a cured material. In contrast to conventional securing means that utilize one or more metal bands placed around the filament ends, the cured material of the present technology extends into the gaps between the bundled filaments and holds them together without adding additional thickness to the braid. In some embodiments, one or more detachment features can be formed into the cured material that beneficially provide a low-profile connection mechanism between the occlusive device and the delivery system. The low-profile securing and detachment means enabled by the cured material can be especially beneficial for use in systems for treating cerebral aneurysms, as the small vessels of the neurovasculature can only be accessed by catheters having an extremely small diameter (e.g., microcatheters).

The subject technology is illustrated, for example, according to various aspects described below, including with reference to FIGS. 2A-11. Various examples of aspects of the subject technology are described as numbered clauses (1, 2, 3, etc.) for convenience. These are provided as examples and do not limit the subject technology.

1. A treatment system comprising:
   a delivery shaft having a proximal portion, a distal portion, and a lumen extending therethrough, wherein the distal portion is configured to be instravascularly positioned proximate an aneurysm;
   a manipulation shaft slidably positioned within the lumen of the delivery shaft, the manipulation shaft having a proximal portion and a distal portion;
   an occlusive device positioned within the lumen of the delivery shaft and coupled to the distal portion of the manipulation shaft, the occlusive device being configured for implantation within the aneurysm, wherein the occlusive device has a proximal end, a distal end, and comprises a plurality of filaments that are secured to one another at the proximal end by a cured material; and
   a detachment element comprising a first end at the distal portion of the manipulation shaft and a second end embedded within the cured material at the proximal end of the occlusive device such that the detachment element couples the manipulation shaft to the occlusive device,
   wherein the detachment element is configured so that application of current through the detachment element causes the detachment element to selectively break between the manipulation shaft and the cured material, thereby decoupling the occlusive device from the manipulation shaft.
2. The treatment system of Clause 1, wherein the manipulation shaft comprises a tubular sidewall, and wherein the detachment element comprises a region of the sidewall having a plurality of longitudinally extending fingers defining a plurality of windows, each window positioned between circumferentially adjacent fingers and comprising an opening extending through the thickness of the sidewall, and wherein the fingers are configured to break upon application of current there-through.

3. The treatment system of Clause 2, wherein the cured material is positioned in at least a portion of each of the windows and covers at least a distal portion of each of the fingers, thereby electrically insulating the covered portions of the fingers.

4. The treatment system of Clause 1, wherein the detachment element comprises an electrically conductive member, and wherein the first end of the electrically conductive member is attached to the distal portion of the manipulation shaft.

5. The treatment system of any one of Clauses 1 to 3, wherein the cured material defines a channel extending therethrough, and wherein the treatment system further comprises an injection shaft positioned within at least a portion of the manipulation shaft and extending distally through the channel.

6. The treatment system of Clause 4, wherein the injection shaft is configured to receive an embolic composition therethrough.

7. The treatment system of Clause 4 or Clause 5, wherein the injection shaft comprises a proximal portion defining a first outer diameter and a first inner diameter, and a distal portion defining a second outer diameter less than the first outer diameter and a second inner diameter less than the first inner diameter, and wherein the proximal portion of the injection shaft terminates distally prior to a proximal edge of the cured material and the distal portion of the injection shaft extends through the channel in the cured material.

8. The treatment system of any one of Clauses 1 to 6, wherein the cured material does not comprise a metal band.

9. The treatment system of any one of Clauses 1 to 7, wherein the cured material comprises a first region with a first diameter and a second region with a second diameter greater than the first diameter, the second region being distal of the first region along a longitudinal axis of the occlusive device.

10. The treatment system of Clause 8, wherein the second end of the detachment element is embedded within the first region of the cured material.

11. The treatment system of any one of Clauses 1 to 9, wherein the occlusive device comprises an inner layer of braided filaments and an outer layer of braided filaments, each comprising proximal end regions, and wherein the proximal end region of the inner layer extends proximally beyond the proximal end region of the outer layer.

12. The treatment system of Clause 10, wherein:

the cured material comprises a first region with a first diameter and a second region with a second diameter greater than the first diameter, the second region being distal of the first region along the longitudinal axis of the occlusive device, the first region of the cured material surrounds and couples the portion of the proximal end region of the inner layer that extends proximally beyond the outer layer, and the second region of the cured material surrounds and secures the proximal end regions of both the inner and outer layers.

13. The treatment system of any one of Clauses 1 to 11, wherein the cured material extends radially between the filaments at the proximal end of the occlusive device.

14. A treatment system comprising:

a delivery shaft comprising a proximal portion, a distal portion, and a lumen extending therethrough, wherein the distal portion is configured to be instravascularly positioned proximate an aneurysm;

a manipulation shaft slidably positioned within the lumen of the delivery shaft, the manipulation shaft comprising a proximal portion and a distal portion;

an occlusive device positioned within the lumen of the delivery shaft and coupled to the distal portion of the manipulation shaft, the occlusive device being configured for implantation within the aneurysm, wherein the occlusive device has a proximal end, a distal end, and a plurality of filaments secured to one another at the proximal end of the occlusive device by a cured material; and a detachment element carried by the distal portion of the manipulation shaft, the detachment element having a first end portion at the manipulation shaft, a second end portion disposed over the filaments at the proximal end of the occlusive device, and a non-insulated region extending therebetween, and wherein the cured material extends over and around the second end portion of the detachment element and the filaments, thereby coupling the manipulation shaft to the occlusive device, wherein the detachment element is configured such that application of current through the detachment element causes the detachment element to selectively break along the non-insulated region, thereby decoupling the occlusive device from the manipulation shaft.

15. The treatment system of Clause 13, wherein the first and second end portions of the detachment element are electrically insulated.

16. The treatment system of Clause 13 or Clause 14, wherein the cured material defines a channel extending therethrough, and wherein the treatment system further comprises an injection shaft that is positioned within at least a portion of the manipulation shaft and extends distally through the channel.

17. The treatment system of Clause 15, wherein the injection shaft is configured to receive an embolic composition therethrough.

18. The treatment system of Clause 15 or Clause 16, wherein the injection shaft comprises a proximal portion defining a first outer diameter and a first inner diameter, and a distal portion defining a second outer diameter less than the first outer diameter and a second inner diameter less than the first inner diameter, and wherein the proximal portion of the injection shaft terminates distally prior to a proximal edge of the cured material and the distal portion of the injection shaft extends through the channel in the cured material.

19. The treatment system of any one of Clauses 13 to 17, wherein the cured material does not comprise a metal band.

20 The treatment system of any one of Clauses 13 to 18, wherein the cured material comprises a first region with a first diameter and a second region with a second diameter greater than the first diameter, the second region being distal of the first region along the longitudinal axis of the occlusive device.

21. The treatment system of Clause 19, wherein the second end of the detachment element is embedded within the first region of the cured material.

22 The treatment system of any one of Clauses 13 to 20, wherein the occlusive device comprises an inner layer of braided filaments and an outer layer of braided filaments, each having proximal end regions, and wherein the proximal end region of the inner layer extends proximally beyond the proximal end region of the outer layer.

23. The treatment system of Clause 21, wherein:

the cured material comprises a first region with a first diameter and a second region with a second diameter greater than the first diameter, the second region being distal of the first region along the longitudinal axis of the occlusive device, the first region of the cured material surrounds and secures the portion of the proximal end region of the inner layer that extends proximally beyond the outer layer, and the second region of the cured material surrounds and secures the proximal end regions of both the inner and outer layers.

24. The treatment system of any one of Clauses 13 to 22, wherein the cured material extends radially between the filaments at the proximal end of the occlusive device.

25. A method comprising:

advancing a delivery system through a vasculature to a treatment site proximate an aneurysm, the delivery system including a delivery shaft, a manipulation shaft positioned within the delivery shaft, and an occlusive device positioned in a collapsed stated within the delivery shaft, wherein the occlusive device comprises a plurality of braided filaments coupled to one another at a proximal end of the occlusive device by a cured material, and wherein the delivery system further comprises a detachment element comprising a first end carried by a distal portion of the manipulation shaft and a second end embedded within the cured material at the proximal end of the occlusive device such that the detachment element couples the manipulation shaft to the occlusive device; and applying a current through the detachment element to electrolytically corrode the detachment element; and severing the electrolytically corroded detachment element in order to detach the occlusive device from the delivery system.

26. The method of Clause 25, wherein the delivery system further comprises an injection shaft having a distal region that extends distally through a channel in the cured material, and wherein the method further comprises delivering an embolic material through the injection shaft while at least a portion of the occlusive device is expanded within the aneurysm.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present disclosure.

In FIG. 2E, the delivery shaft and injection shaft have been removed for ease of illustration.

In FIG. 4, the system is shown in a secured delivery configuration.

In FIG. 5, the system is shown at an intermediate stage of releasing the implant.

In FIG. 7, the system is shown in a secured delivery configuration.

In FIG. 8, the system is shown at an intermediate stage of releasing the implant.

In FIG. 10, the system is shown in a secured delivery configuration.

In FIG. 11, the system is shown at an intermediate stage of releasing the implant.

DETAILED DESCRIPTION

The present technology is directed to devices, systems, and methods for delivering an occlusive device and an embolic fluid to a treatment location in a blood vessel (such as an aneurysm). In some embodiments, the technology comprises delivering the occlusive device to a treatment location via a delivery system and, before detaching the occlusive device from the delivery system, delivering the embolic fluid through a proximal end of the occlusive device into the aneurysm. In order to preserve a large internal diameter through the occlusive device (to reduce the pressure required to push the embolic fluid), it is beneficial to minimize the number and/or size of components at the proximal end. This can be especially difficult, however, when the occlusive device comprises a plurality of braided and/or woven filaments. The free ends of the filaments need to be constrained so that the braid does not unravel and to prevent breaking or damage to individual filaments within the delivery system or once deployed in the aneurysm.

Figure 1:
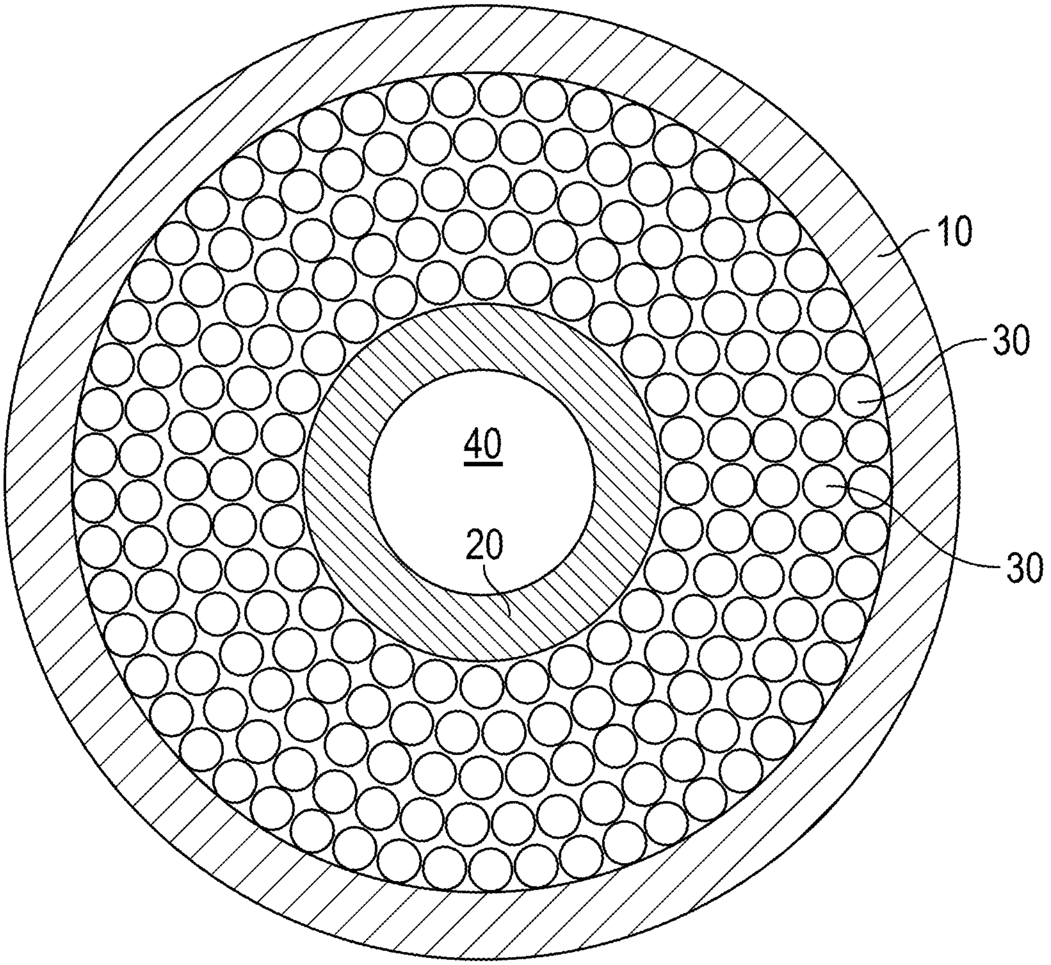
FIG. 1 (Prior Art)
FIG. 1 is an axial cross-sectional view of a secured portion of an occlusive device of the prior art.

Conventional methods for constraining the free ends while maintaining a central lumen typically include sandwiching the filament ends between two metal bands. An example of such a prior art assembly is shown in the axial cross-sectional view of FIG. 1. The filament ends 30 are positioned between an outer metal band 10 and an inner metal band 20, and a lumen 40 extends through and is defined by the inner metal band 20. One of the drawbacks of this method is that the space occupied by the metal bands reduces the diameter of the flow channel for the embolic fluid. For example, the minimum wall thickness of each band ranges from 0.001-0.002 inches, which results in a buildup of a minimum of 0.002-0.004 inches through one side of the bands. Together the inner and outer bands thus occupy a minimum of 0.004-0.008 inches, which is approximately 25-50% of the total available space in, for example, a delivery catheter having a 0.017 inner diameter (which is the smallest existing commercial microcatheter).

To reduce the buildup of wall thicknesses or additional components inside of the delivery catheter, the occlusive devices of the present technology are secured at their proximal ends by a cured material and do not include any bands or other mechanical restraints. The cured material may add only a nominal amount to the overall thickness/diameter of the bundled filaments, thus providing 25-50% more space within the delivery catheter (relative to bands) that can be used to enlarge the fluid channel running through the secured filament ends. The cured material provides the additional advantage of being moldable to include one or more features that engage with the delivery system to facilitate detachment of the occlusive device, as described in greater detail below.

I. Overview of Treatment Systems of the Present Technology

Figures 2A, 2B:
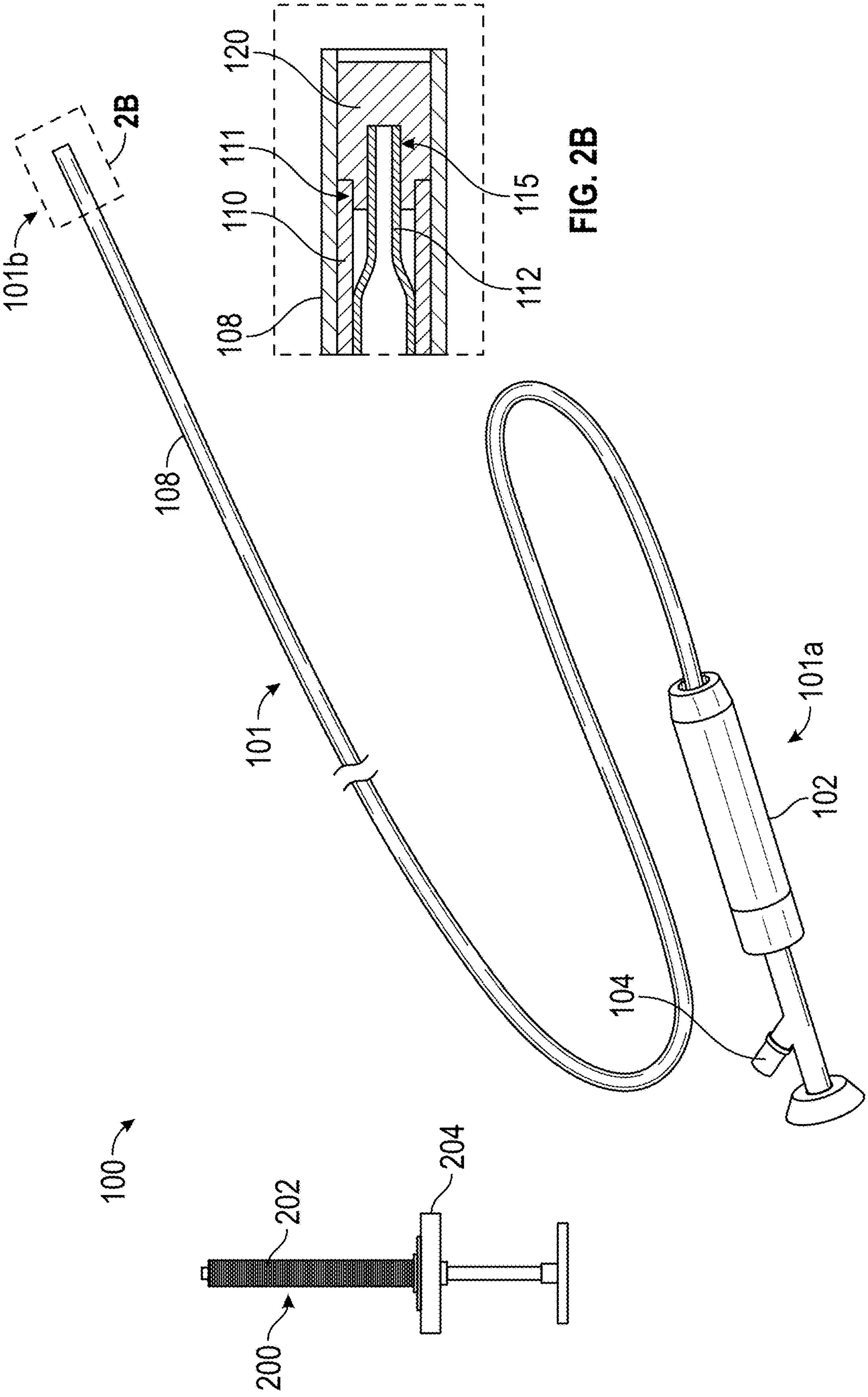
FIG. 2A is a partially schematic view of a system for treating an aneurysm in accordance with embodiments of the present technology.
FIG. 2B is a partially schematic enlarged cross-sectional view of a distal portion of the system shown in FIG. 2A.

FIG. 2A shows a system 100 for treating aneurysms, such as cerebral aneurysms, according to one or more embodiments of the present technology. FIG. 2B is an enlarged cross-sectional view of the distal portion of the system 100. As shown in FIGS. 2A and 2B, the system 100 comprises a delivery system 101, an occlusive device 120 (shown in a collapsed delivery configuration), and an embolic kit 200. In some embodiments the system 100 does not include the embolic kit 200. The occlusive device 120 is configured to be detachably coupled to the delivery system 101, and the delivery system 101 is configured to intravascularly position the occlusive device 120 within an aneurysm. The occlusive device 120 can have a collapsed configuration for delivery through a catheter to the aneurysm (as shown in FIG. 2B) and an expanded, deployed state for implantation in the aneurysm cavity.

The embolic kit 200 can comprise an embolic composition 202 and an injector device 204 ("injector 204") configured to be fluidly coupled to a proximal portion of the delivery system 101 for injection of the embolic composition 202 into the aneurysm cavity. The embolic composition 202 can be delivered to a space between the occlusive device 120 and the dome of the aneurysm to fill and occlude the aneurysm cavity. Additionally or alternatively, the embolic composition 202 can be delivered to an interior region of the occlusive device 120 once the occlusive device 120 has been at least partially deployed in the aneurysm. The occlusive device 120 prevents migration of the embolic composition 202 into the parent vessel, and together the occlusive device 120 and embolic composition 202 prevent blood from flowing into the aneurysm. Bioabsorption of the embolic composition 202 and endothelialization of the occlusive device 120 cause the aneurysm wall to fully degrade, leaving behind a successfully remodeled (aneurysm free) region of the blood vessel.

The embolic composition 202 can be any material suitable for forming a solid or semi-solid structure (e.g., a hydrogel) that partially or completely occludes the interior cavity of the aneurysm. For example, the embolic composition 202 can include one or more polymers, such as a synthetic polymer (e.g., poly (glycolide), poly (lactide), poly (vinyl alcohol)), a biopolymer (e.g., chitosan, gelatin, silk, cellulose, alginate, hyaluronic acid), or a combination thereof. The embolic composition 202 can optionally include one or more components to facilitate gelation and/or enhance storage stability, such as cross-linking agents, stabilizers, thickeners, spacers, etc. Optionally, the embolic composition 202 can include a contrast agent to enable visualization (e.g., iohexol, iopromide, ioversol, iopamidol, iodixanol, ioxilan, iothalamate/meglumine, ioxaglate/meglumine, diatrizoate/meglumine). The embolic composition 202 can be biodegradable or non-biodegradable.

Referring still to FIGS. 2A and 2B, the delivery system 101 has a proximal portion 101*a* configured to be extracorporeally positioned during treatment and a distal portion 101*b* configured to be intravascularly positioned at or within an aneurysm. The delivery system 101 may include a handle 102 at the proximal portion 101*a* and a plurality of elongated shafts extending between the handle 102 and the distal portion 101*b*. For example, the delivery system 101 may include a delivery shaft 108 (such as a microcatheter) and a manipulation shaft 110 (FIG. 2B) configured to be slidably disposed within a lumen of the delivery shaft 108. The system 101 may optionally include an injection shaft 112 (FIG. 2B) configured to be disposed within a lumen of the manipulation shaft 110. In such embodiments, the injection shaft 112 can be slidably disposed within the lumen of the manipulation shaft 110, or the manipulation and injection shafts 110, 112 are fixed to one another. The delivery system 101 and/or the manipulation shaft 110 is configured to be detachably coupled at its distal end portion to the occlusive device 120, as described in greater detail below with reference to FIGS. 3-8.

The manipulation shaft 110 can have a proximal portion at the handle 102 and a distal portion 111 that is configured to releasably engage a portion of the occlusive device 120 to secure the occlusive device 120 to the delivery system 101. The manipulation shaft 110 can be movable within the delivery shaft 108 to position the occlusive device 120 at a desired location. The manipulation shaft 110 can be sufficiently flexible to enable manipulation, e.g., advancement and/or retraction, of the occlusive device 120 through tortuous passages.

The injection shaft 112 can have a proximal portion at the proximal portion 101*a* of the delivery system 101 (e.g., at the handle 102) and a distal portion 115 that terminates within the occlusive device 120, as shown in FIG. 2B. The proximal portion of the injection shaft 112 is configured to be fluidly coupled to the injector 204 (for example, via a port 104 on the handle 102) or other device containing the embolic composition 202. Pressure generated at the injector 204 causes the embolic composition 202 to flow through the lumen of the injection shaft 112 and into a space distal of the proximal end of the occlusive device 120, for example to an interior region of the occlusive device 120 or to a space between a portion of the occlusive device 120 and the aneurysm dome. Once the embolic composition 202 has sufficiently filled the aneurysm cavity and/or occlusive device 120, the occlusive device 120 can be detached from the delivery system 101. The delivery system 101, including the injection shaft 112, can then be withdrawn from the treatment site. In some embodiments, the lumen of the injection shaft 112 can be configured to receive a guidewire therethrough.

In some embodiments, the injection shaft 112 does not extend proximally back to the proximal portion 101*a* of the delivery system 101 and instead terminates proximally at an intermediate location along the lumen of the manipulation shaft 110. For example, the injection shaft 112 can be an extension tube (not shown) that is attached to the distal end of the manipulation shaft 110. A proximal end of the injection shaft 112 can reside, and be fixed to, an inner surface of the manipulation shaft 110 that defines the manipulation shaft lumen, and a distal end of the injection shaft 112 extends beyond the distal end of the manipulation shaft 110. In such embodiments, the proximal portion of the manipulation shaft 110 can be configured to be fluidly coupled to the injector 204 (or other source of the embolic composition 202), and the lumen of the manipulation shaft 110 can be configured to receive the embolic composition and transfer the embolic composition to the injection shaft 112.

Figure 2C:
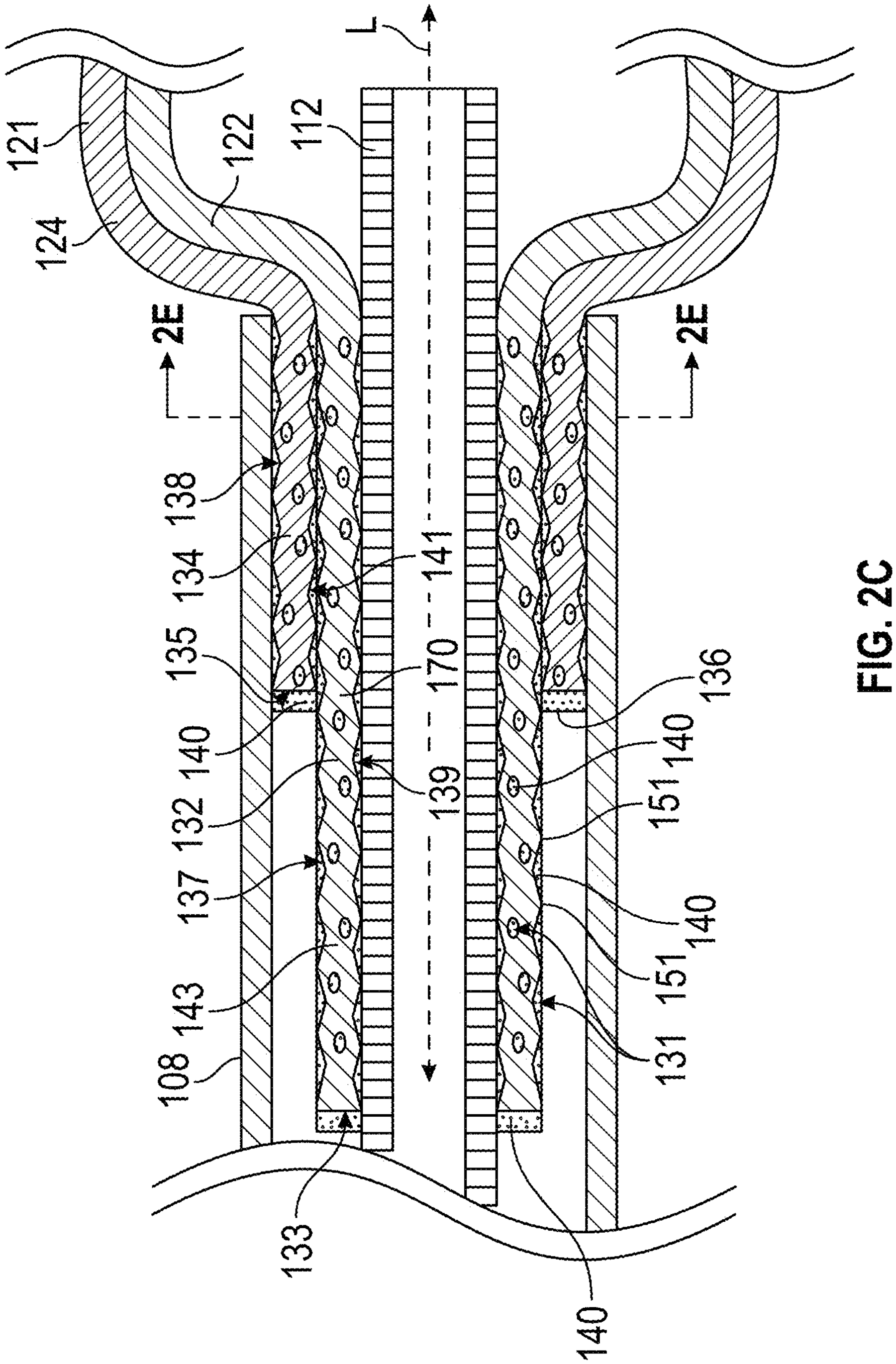
FIG. 2C is a partially schematic view of the proximal portion of an occlusive device engaged with a delivery system configured in accordance with several embodiments of the present technology.

FIG. 2C shows a cross-sectional view of a portion of the occlusive device 120. The occlusive device 120 is shown partially deployed in FIG. 2C with a proximal portion remaining within the delivery shaft 108 and the occlusive device 120 remains coupled to the delivery system 101. The manipulation shaft 110 has been removed in FIG. 2C for ease of illustration. The occlusive device 120 can comprise a resilient mesh 121 formed of a plurality of braided and/or woven filaments that have been shape set to assume a desired three-dimensional shape when unconstrained (e.g., released from the delivery shaft 108). The mesh 121 can have any shape or size in the expanded state that enables the mesh 121 to cover the aneurysm neck, and a porosity sufficient to prevent leakage of the embolic composition 202 into the parent vessel. Representative examples of meshes that are suitable for use with the system 100 are described in U.S. Pat. Nos. 8,142,456, 9,855,051, 10,327,781, U.S. Patent Application Publication No. 2020/0187953, U.S. Patent Application Publication No. 2021/0128169, U.S. Patent Application and U.S. Publication No. 2021/0153872, and Application No. 63/369,936, filed Jul. 30, 2022, and titled OCCLUSIVE DEVICES FOR TREATING VASCULAR DEFECTS AND ASSOCIATED SYSTEMS AND METHODS, the disclosures of which are incorporated by reference herein in their entireties.

The mesh 121 may be formed of metal wires, polymer wires, or both, and the wires may have shape memory and/or superelastic properties. The mesh 121 may be formed of 24, 32, 36, 48, 64, 72, 96, 128, or 144 filaments. The mesh 121 may be formed of a range of filament or wire sizes, such as wires having a diameter of from about 0.0004 inches to about 0.0020 inches, or of from about 0.0009 inches to about 0.0012 inches. In some embodiments, each of the wires or filaments have a diameter of about 0.0004 inches, about 0.0005 inches, about 0.0006 inches, about 0.0007 inches, about 0.0008 inches, about 0.0009 inches, about 0.001 inches, about 0.0011 inches, about 0.0012 inches, about 0.0013 inches, about 0.0014 inches, about 0.0015 inches, about 0.0016 inches, about 0.0017 inches, about 0.0018 inches, about 0.0019 inches, or about 0.0020 inches.

As best shown in FIG. 2C, in some embodiments the mesh 121 can comprise inner and outer layers 122, 124, each comprising a plurality of braided and/or woven filaments. The inner and outer layers 122, 124 can have respective proximal end regions 132, 134 that come together at a proximal region of the occlusive device 120. The distal ends of the inner and outer layers 122, 124 (not shown) may be attached to one another at the distal end of the occlusive device 120, or may be secured separately and/or spaced apart from one another.

Each of the proximal end regions 132, 134 terminates proximally at a respective proximal terminus 133, 135. As shown in FIG. 2C, in some embodiments the first and second proximal end regions and/or termini are staggered along the longitudinal axis L of the device 120 such that the proximal terminus 133 of the inner layer 122 is proximal of and spaced apart from the proximal terminus 135 of the second or outer layer 124. As such, the proximal end region 132 of the inner layer 122 can include an exposed portion 143 that does not radially overlap the proximal end region 134 of the outer layer 124 and a covered portion 170 that radially overlaps the proximal end region 134 of the outer layer 124. In some embodiments, the proximal terminus 135 of the outer layer 124 is proximal of and spaced apart from the proximal terminus 133 of the inner layer 122.

Figure 2D:
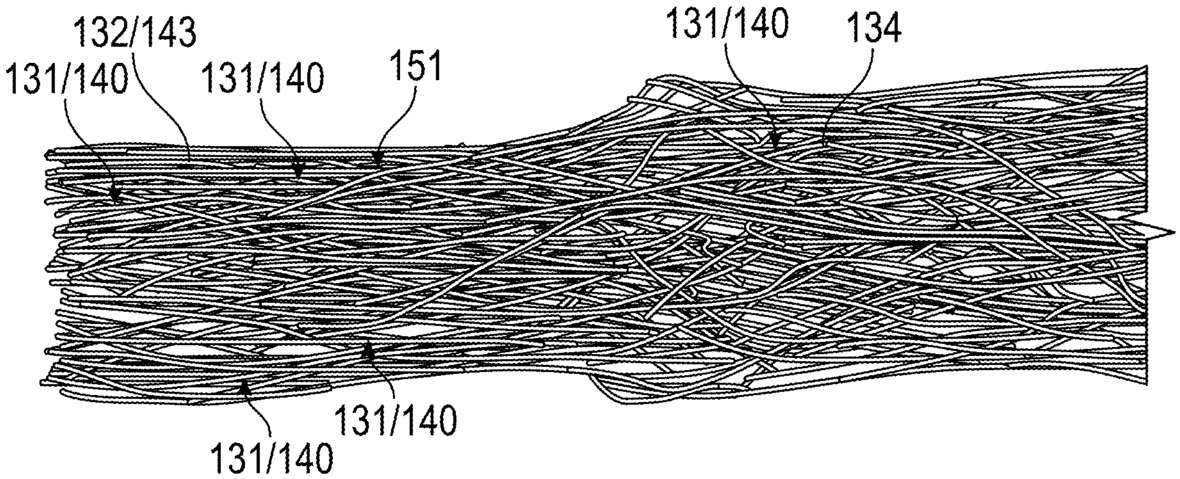
FIG. 2D is a photograph showing the proximal regions of the inner and outer layers as secured by a cured material in accordance with several embodiments of the present technology.

The occlusive device 120 can further include a cured material 140 that extends between and holds together the filaments of the first and second proximal end regions 132, 134 of the inner and outer layers 122, 124. For example, as shown in FIGS. 2C and 2D, the cured material 140 can be disposed within and/or fill the interstices 131 between the filaments comprising the mesh 121 such that the filaments and the cured material 140 together form a composite structure at the proximal end of the occlusive device 120. The cured material 140 can be applied to the proximal end regions 132, 134 in a flowable form (e.g., via insert molding, overmolding, injection molding, reflow, etc.) that beneficially allows for the material to flow into and/or through the interstices between the layers and/or filaments, and also allows for control of the final shape and thickness of the cured material 140.

Figure 2E:
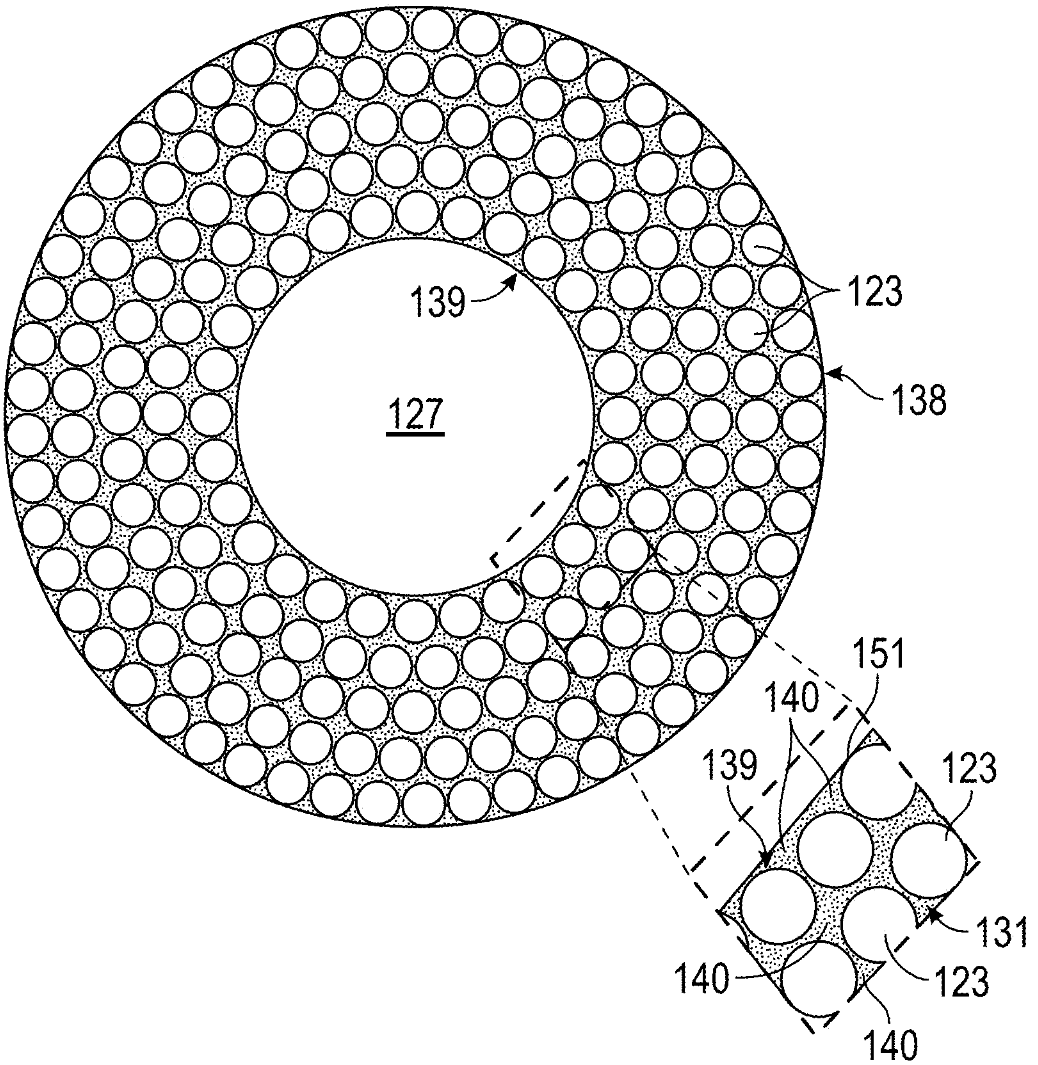
FIG. 2E is a cross-sectional axial view taken along line 2E-2E in FIG. 2C.

Depending on the delivery system requirements and method of manufacturing, the cured material 140 may be confined to the spaces 131 under and between the outermost surfaces 151 (FIGS. 2D and 2E) of the bundled filaments 123 and generally may not be disposed over and/or on the outermost surfaces 151 (for example, if the outermost surfaces 151 are in contact with a mold or other element during an insert molding or reflow process). In some embodiments, the cured material 140 is disposed within the spaces 131 under and between the outermost surfaces 151 (FIGS. 2D and 2E) of the bundled filaments 123 and over and/or on the outermost surfaces 151 along all or a portion of a radially outer surface 138 of the proximal end region 134 of the outer layer 124, a radially outer surface 137 of the proximal end region 132 of the inner layer 122, a radially inner surface 139 of the inner layer 122, a radially inner surface 141 of the outer layer 124, and/or over each of the proximal termini 133, 135.

According to several aspects of the present disclosure, for example as shown in FIGS. 2C and 2D, in some embodiments the cured material 140 is disposed only within the interstices 131 (shown schematically) between adjacent filaments 123 (FIG. 2D), which includes gaps between filaments along the individual layers as well as at the interface between the radially outer surface 137 of the inner layer 122 and the radially inner surface 138 of the outer layer 124 where the inner and outer layers 122, 124 overlap. In several of such embodiments, the cured material 140 is not disposed on the outer surface 137 of the exposed portion 143 of the inner layer 122, the radially outer surface 138 of the outer layer 124, and/or the radially inner surface 139 of the inner layer 122. While the cured material 140 may exist at or near the radially outer surface of the foregoing portions by filling in gaps 131 between filaments at the respective surface, the cured material 140 does not form a layer of material over the filaments. In these and other embodiments in which the cured material 140 does not form a layer over the radially inner surface of the inner layer 122, the outermost filament surfaces 151 and the cured material 140 between the outermost filament surfaces 151 together define a lumen 127 (FIG. 2E) extending through the secured proximal end regions 132, 134 and through which the injection shaft 112 can be positioned. In contrast to the bands of the prior art (see FIG. 1), the proximal end regions 132, 134 of the filaments of the present technology are secured without adding to the existing outer diameter defined by the bunched filaments and without taking away from the inner diameter extending through the bunched filaments.

Figure 2F:
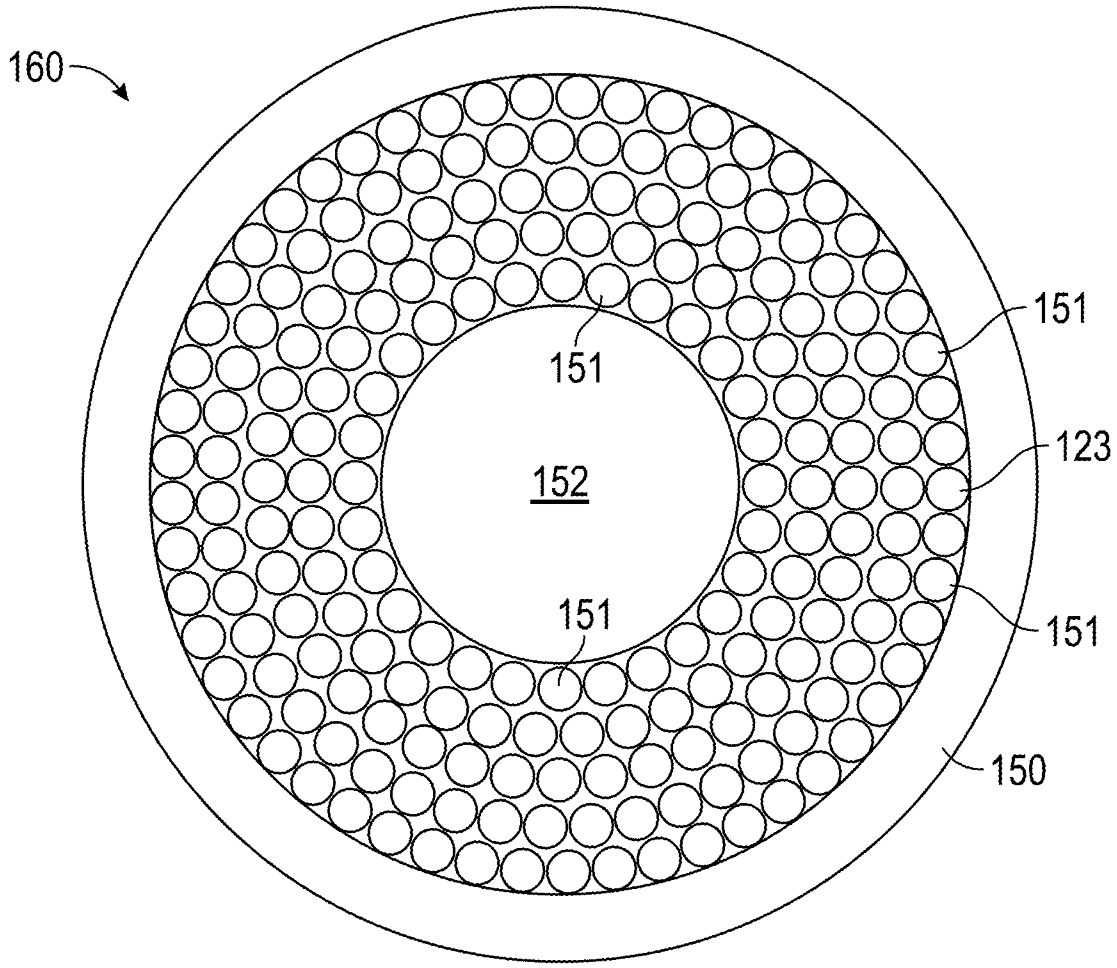
FIG. 2F is a cross-sectional axial view of a mold assembly configured in accordance with several embodiments of the present technology.

According to some embodiments, the composite structure shown in FIGS. 2C and 2D can be formed by an overmolding process, such as insert molding, injection molding, etc. As shown in FIG. 2F, the mold assembly 160 can comprise an outer member 150 having a lumen that approximates what will be the outer diameter of the composite structure and an inner member 152 having an outer diameter that approximates what will be the outer diameter of the injection shaft 112. The proximal end regions 132, 134 can be inserted into the mold, between the outer and inner members 150, 152, and the liquid form of the cured material can be injected between the outer and inner members 150, 152 and allowed to cure (e.g., harden, solidify, etc.). As demonstrated by FIGS. 2E and 2F, because the filaments 123 are sandwiched tightly between the outer member 150 and the inner member 152, the portions of the surfaces of the filaments that are pressed against the outer or inner member 150, 152 (such as outermost surfaces 151, only a few labeled) may not have any cured material 140 thereon when the filaments 123 are removed from the mold. The material can be any suitable curable material, such as an injectable adhesive, liquid plastic, and/or other composite material. In some embodiments, the material is a UV-curable epoxy. In some embodiments, the cured material 140 is a monolithic body.

Figure 2G:
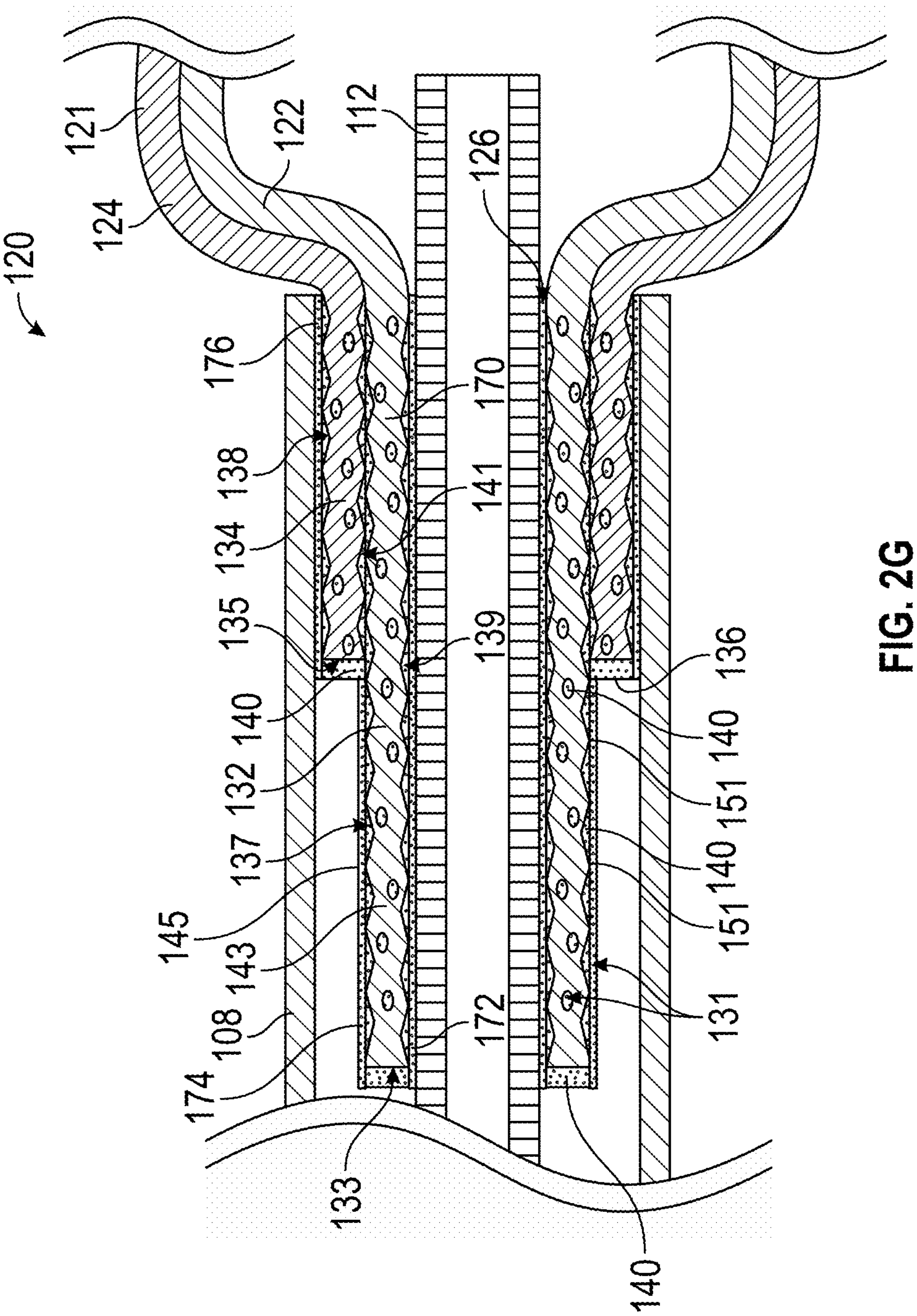
FIG. 2G is a partially schematic view of the proximal portion of an occlusive device engaged with a delivery system configured in accordance with several embodiments of the present technology.

Referring to FIG. 2G, in some embodiments the cured material 140 forms at least one of a first layer 176 on and along all or a portion of a radially outer surface 138 of the proximal end region 134 of the outer layer 124, a second layer 174 on and along all or a portion of a radially outer surface 137 of the proximal end region 132 of the inner layer 122, and/or a third layer 172 on and along all or a portion of a radially inner surface 139 of the inner layer 122. The layers 172, 174, and 176 can be disposed on top of the outermost surfaces 151 of the filaments and the cured material 140 within interstices 131. In such embodiments in which the cured material 140 forms a layer 172 over the radially inner surface of the inner layer 122 along the proximal end region 132, the cured material 140 defines a lumen 126 extending through the secured proximal end regions 132, 134 and through which the injection shaft 112 can be positioned. In contrast to a conventional metal band, the cured material 140 can conform to the step created by the staggered proximal ends 132, 134.

According to some methods of manufacturing, the layers of the composite structure of FIG. 2G can be formed by reflowing a solid material over the filaments. The solid material can be a thermoplastic material, such as Pebax®, polyolefin, polyvinyl chloride (PVC), a fluoropolymer, polytetrafluoroethylene (PTFE), fluorinated ethylene propylene (FEP), Kynar®, Viton®, and/or others. In some embodiments, a first layer of solid material (in the form of a wrap, a tube, strips, etc.) can be placed on the outer surface of the inner member 152 (see FIG. 2F) of the mold and the inner and outer layers 122, 124 are placed over the first layer. A second layer of solid material (in the form of a wrap, a tube, strips, etc.) can be placed over the proximal end regions of the inner and outer layers 122, 124 and a shrink tube (e.g., PTFE, etc.) is placed over the entire assembly. Heat is then applied to the assembly so that the shrink tube generates a radial inward force while the thermoplastic layers melt into the voids of the braid, which once hardened creates a composite structure comprising the filaments and the cured material.

The finished assembly includes a layer of cured material 140 on the radially outer surface 138 of the outer layer 124 (formed by reflowing the second layer) and a layer of cured material 140 on the radially inner surface of the inner layer 122 (formed by reflowing the first layer). In some embodiments, other techniques can be used to form one, some, or all of the layers 172, 174, 176, such as an overmolding process that utilizes a standoff between the filaments and the mold surfaces.

Referring to FIG. 2G, because of the staggered arrangement of the proximal end regions 132, 134 of the mesh 121, an outer diameter of the composite structure along the second layer 174 of the cured material 140 is greater than an outer diameter of the composite structure along the second region 144, thereby forming a shelf 145 in the cured material 140. The shelf 145 can be defined by the second layer 174 and a proximally facing annular surface 136 formed by the step between the second and first layers 174, 176. As detailed below, the shelf 145 formed by the cured material 140 can be engaged by the manipulation shaft 110 (FIG. 2B) to secure the occlusive device 120 to the manipulation shaft 110 and/or as leverage to push the occlusive device 120 out of the manipulation shaft 110.

It will be appreciated that the cured material 140 can be used with single-layer occlusive devices as well as multi-layer occlusive devices without staggered proximal ends (i.e., with aligned proximal ends). While the topography created by the staggered mesh layers can help in forming the shelf 145 in the cured material 140, the cured material 140 can be molded during manufacture to include any shape, including a shelf 145, regardless of the underlying mesh topography. Moreover, in any of the foregoing embodiments, the cured material 140 can be loaded with radiopaque materials, such as barium sulfate, bismuth subcarbonate, and the like to enhance intra-operative visualization.

II. Selected Embodiments of Detachment Regions and Methods of Use

Figure 3:
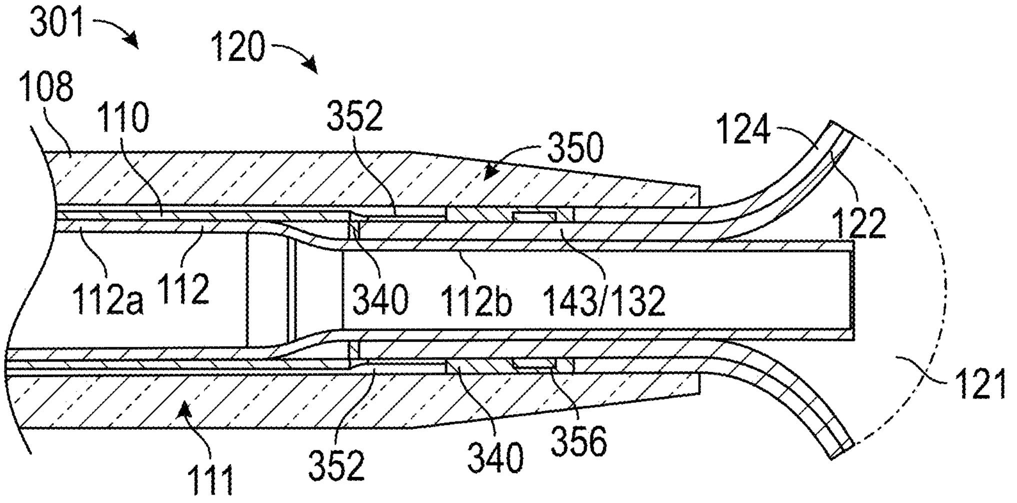
FIG. 3 is a cross-sectional view of a distal portion of a system for treating an aneurysm in accordance with embodiments of the present technology.
Figure 4:
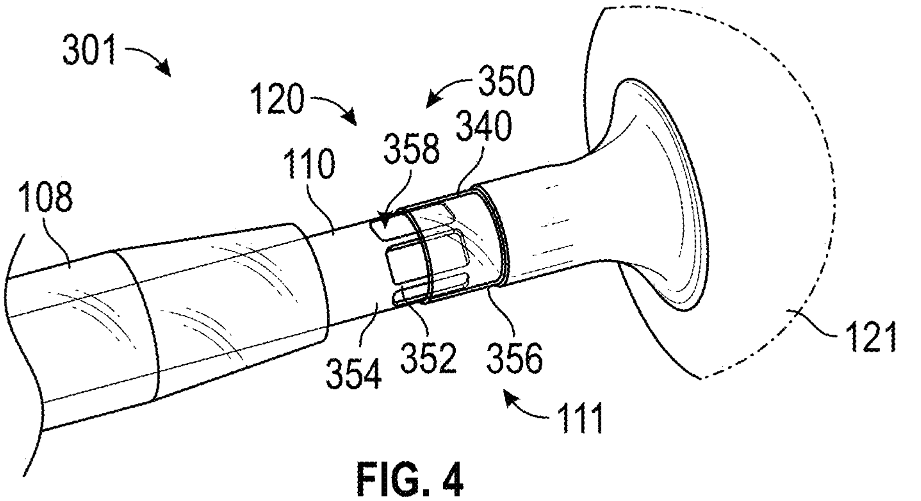
FIG. 4 is a partially transparent, perspective view of the distal portion shown in FIG. 3.
Figure 5:
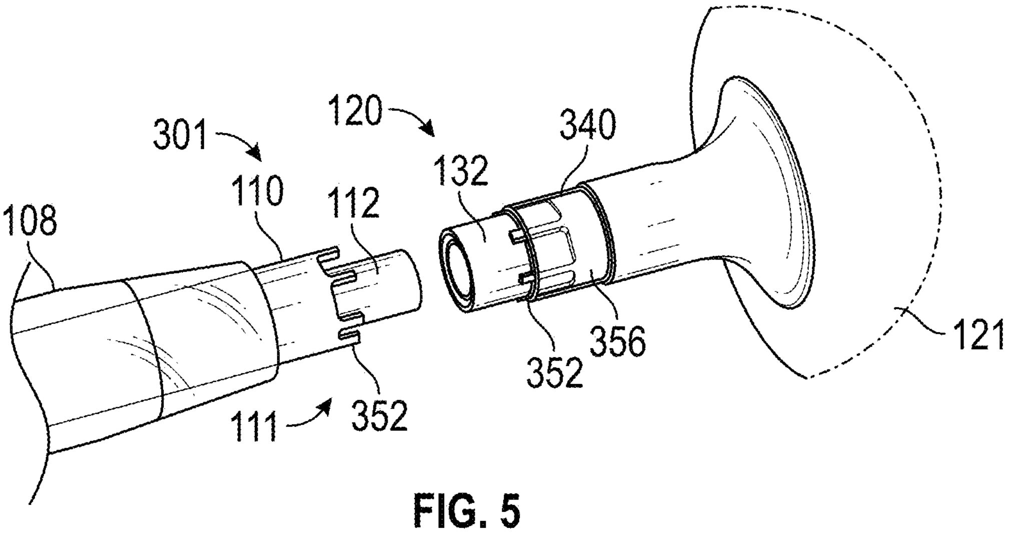
FIG. 5 is a partially transparent, perspective view of the distal portion shown in FIG. 3.

The cured material 140 of the present technology can be configured to engage with one or more components of the delivery system 101 to releasably secure the occlusive device 120 to the delivery system 101. For example, in some embodiments the delivery system includes an electrolytic detachment element at least partially embedded within the cured material 140 that couples the occlusive device 120 to the manipulation shaft 110. According to some embodiments, the detachment element is formed from a distal portion of the sidewall of the manipulation shaft 110. For example, FIGS. 3-5 show a delivery system 301 having the same features and components as the delivery system 101, except the distal portion 111 of the manipulation shaft 110 of delivery system 301 includes a detachment zone 350 that is at least partially embedded within a cured material 340 at the proximal end of the occlusive device 120. The detachment zone 350 is configured to electrolytically corrode and break when current is applied to the manipulation shaft 110, as detailed below. The cured material 340 can have the same features as the cured material 140 discussed above with reference to FIGS. 2A-2G except as noted in the following discussion. For case of illustration, the inner and outer layers are shown in FIGS. 3-11 as solid blocks without the interstices and cured material as shown schematically in FIGS. 2C and 2G. It will be appreciated that the cured material and filaments of FIGS. 3-11 can form any of the composite structure variations detailed above with reference to FIGS. 2C-2G.

The delivery system 301 can include a power supply (not shown), and a proximal portion of the manipulation shaft 110 can be configured to be electrically coupled to the power supply. The manipulation shaft 110 (and thus the detachment zone 350) can comprise an electrolytically corrodible material. The power supply may also be coupled to a proximal portion of the handle 102 (FIG. 2A) or to the patient. A current can flow from the power supply through the manipulation shaft 110 to the detachment zone 350, and to a return path via the delivery shaft 108, the injection shaft 112, and/or another structure extending near the detachment zone 350. Alternatively, the current from the detachment zone 350 may flow to the patient, and subsequently to ground or to the power supply. The power supply, for example, can be a direct current power supply, an alternating current power supply, or a power supply switchable between a direct current and an alternating current. In some embodiments, a positive terminal of a direct current power supply may be coupled to the proximal portion of the manipulation shaft 110 and a negative terminal of a direct current power supply may be coupled to the proximal portion of the handle 102. The power supply may provide a current through the treatment system to initiate an electrolytic process during use of the system 301 in a fluid medium such as a bloodstream, which may be used as an electrolyte.

The detachment zone 350 can comprise a distal portion 111 of the manipulation shaft 110 along which portions of the sidewall have been removed to form a plurality of longitudinally extending fingers 352 disposed about the circumference of the manipulation shaft 110 and spaced apart by individual windows 358 (where the sidewall has been removed). In some embodiments, the sidewall of the manipulation shaft 110 may be electrically insulated along its length except at the fingers 352. All or a portion of each of the fingers 352 can be non-insulated so that current applied through the manipulation shaft 110 selectively targets the fingers 352 for electrolytic corrosion. Each of the fingers 352 can extend between a proximal end at a proximal circumferentially continuous portion 354 of the manipulation shaft 110 and a distal end at a distal circumferentially continuous portion 356 of the manipulation shaft 110 (also referred to as "distal band 356"). The distal band 356 can beneficially provide more surface area for the cured material 340 to grip (relative to embodiments with only the fingers 352 and no distal band 356). In some embodiments, the detachment zone 350 does not include the distal band 356 and instead the fingers 352 remain unconnected at their distal ends. In any case, the fingers 352 can have individual thicknesses (measured in a circumferential direction) that are less than the individual thicknesses of the windows 358. The fingers 352 can be sufficiently thick to withstand and transfer the deployment and resheathing forces exerted on the occlusive device 120 by the manipulation shaft 110, yet sufficiently thin such that upon application of a current through the manipulation shaft 110, the portion of the fingers 352 proximal of the cured material 340 electrolytically dissolve, thereby breaking the connection between the manipulation shaft 110 and the occlusive device 120. Although six fingers 352 are shown in FIGS. 3-5, the manipulation shaft 110 can have any number of fingers 352 (e.g., one finger, three fingers, four fingers, five fingers, six fingers, etc.).

At least a distal length of the fingers 352 and the distal band 356 can be embedded within, and insulated by, the cured material 340. For example, the detachment zone 350 of the manipulation shaft 110 can be positioned on the exposed portion 143 of the proximal end region 132 of the inner layer 122 (labeled in FIGS. 3 and 5) which may or may not have a second layer 174 of cured material 340 thereon. As previously explained, regardless of whether a continuous layer of cured material 340 is present, the exposed portion 143 of the proximal end region 132 of the inner layer 122 will still have some cured material at its boundary as the cured material 340 fills the interstices of the braided filaments. As such, a radially inner surface of the detachment zone 350/manipulation shaft 110 can be in contact with a radially outer surface of the second layer 174 of cured material 340 (not shown), or in contact with a composite structure composed of the filaments and cured material extending therebetween. The cured material 340 can be thick enough to extend over the distal band 356 and over and between at least a distal portion of the fingers 352 (e.g., thereby embedding the distal portion of the fingers 352 in the cured material 340). Thus, the cured material 340 can be disposed at least on the radially outer surface of the fingers 352 as well as within a portion of the windows 358 to cover a portion of the lateral surfaces of the fingers 352. In some embodiments, the composite structure also includes a cured material layer between the proximal end region 132 of the inner layer 122 and the radially inner surface of the detachment zone 350 and/or fingers 352.

According to some methods of manufacturing, the detachment zone 350 of the manipulation shaft 110 can be insert molded with the proximal ends of the filaments of the mesh 121 of the occlusive device 120. For example, the proximal ends of the filaments and the distal tip of the manipulation shaft 110 (that contains a portion of the detachment zone 350) can be loaded into a mold and then be overmolded with a thermoplastic resin (or other flowable precursor) to form the cured material 340 around the inserted materials. In some embodiments, the mold assembly includes placeholder elements to exclude the curable material from flowing into the proximal portions of the windows (thereby leaving at least the proximal portions of the fingers 352 electrically exposed).

According to some embodiments, the detachment zone 350 and cured material 340 can be assembled by reflowing a solid material (such as a thermoplastic or others, as detailed above). In such embodiments, a first layer of thermoplastic material can be placed onto a mandrel of having an outer diameter corresponding to the finished inner diameter of the secured assembly. The inner and outer layers of braid can be placed over the first layer of material. The distal portion of the manipulation shaft can be positioned over the exposed portion of the inner layer of braid and approximated to the proximal end of the outer layer of the braid. A second layer of thermoplastic material can then be positioned over the assembly such that it covers the distal portions (and not the entire lengths) of the fingers 352, the distal band 356, and the proximal end region of the outer layer. A shrink tube (such as PTFE) can be placed over the entire length of assembly, which includes the proximal ends of the fingers 352. Heat can then be applied to the mold, causing the shrink tube to shrink and generate a radial inward force while the thermoplastic layers melt into the voids of the braid. Once the material has solidified to form the cured material, the shrink tube can be removed.

According to some methods of use, the distal portion of the delivery system 301 can be positioned proximate an aneurysm and the occlusive device 120 can be pushed distally (via the manipulation shaft 110) beyond a distal end of the delivery shaft 108 and into the aneurysm. Release of the occlusive device 120 from the delivery shaft 108 allows the mesh 121 of the occlusive device 120 to self-expand. During and/or after deployment of the occlusive device 120, the embolic composition 202 (FIG. 2A) can be delivered into the aneurysm cavity through the injection shaft 112 extending through the cured material 340. To detach the occlusive device 120 from the delivery system 301, current can be applied to the manipulation shaft 110 to electrolytically corrode the non-insulated portions of the fingers 352 of the detachment zone 350. Prior to application of the current, the delivery shaft 108 can be withdrawn proximally beyond the detachment zone 350 (if not already) to place the non-insulated portions of the fingers 352 (e.g., proximal of the proximal edge of the cured material 340) in contact with the bloodstream so that the blood can serve as an electrolyte for the electrolytic corrosion of the fingers 352. After the fingers 352 have been severed at the detachment zone 350 (as shown in FIG. 5), the manipulation shaft 110 and injection shaft 112 can be retracted and the occlusive device 120 may remain in position within the aneurysm.

Because the inner diameter of the manipulation shaft 110 is greater than the inner diameter of the channel extending through the cured material 340, the outer diameter of the injection shaft 112 can be tapered proximally. In some embodiments, both the outer diameter and the inner diameter of the injection shaft 112 can be tapered proximally. For example, as shown in FIG. 3, the injection shaft 112 can have a first, more proximal portion 112*a* having first outer and inner diameters, and a second, more distal portion 112*b* having second outer and inner diameters that are less than the outer and inner diameter, respectively, of the first portion 112*a*. In some embodiments, the injection shaft 112 can have a constant inner and/or outer diameter along its length. For example, the injection shaft 112 shown in FIGS. 6-8 (discussed below) has a constant inner and outer diameter.

Figure 6:
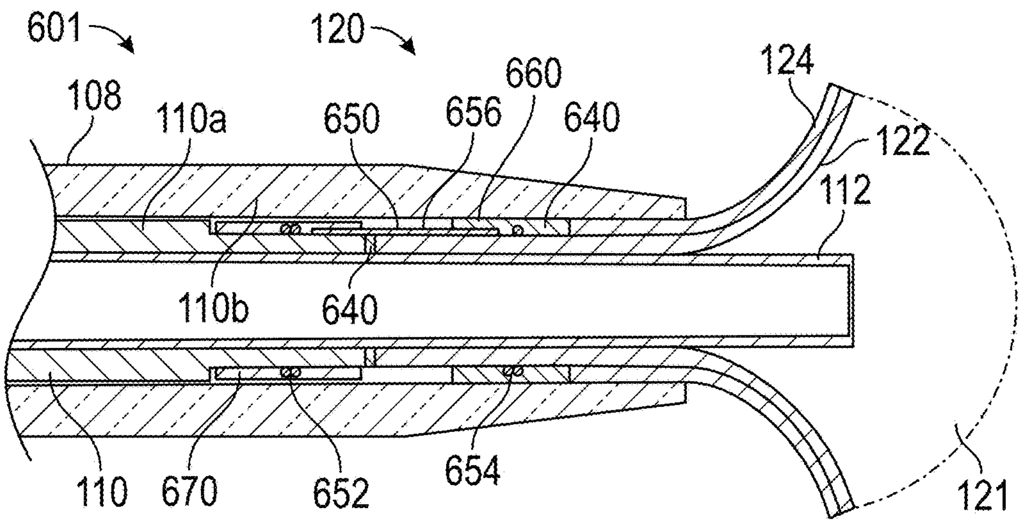
FIG. 6 is a cross-sectional view of a distal portion of a system for treating an aneurysm in accordance with embodiments of the present technology.
Figure 7:
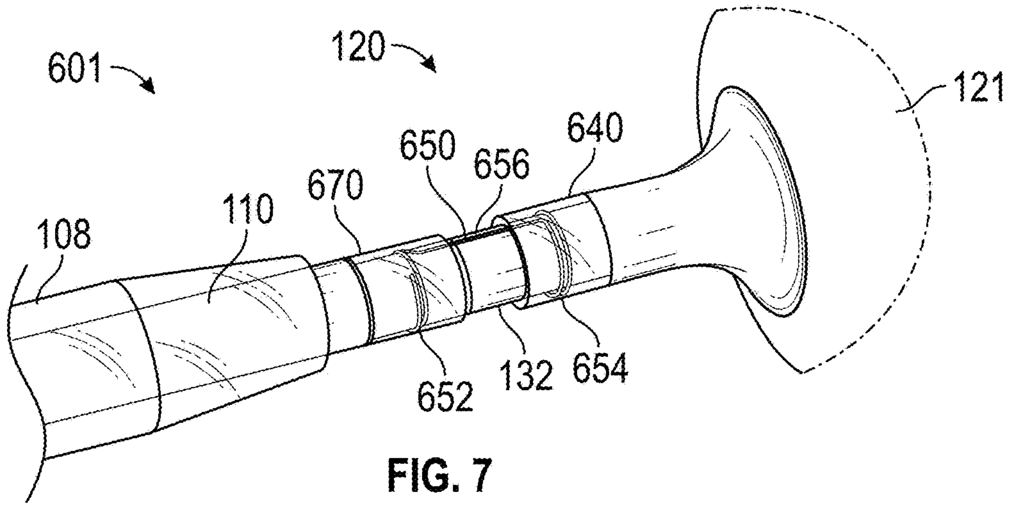
FIG. 7 is a partially transparent, perspective view of the distal portion shown in FIG. 6.
Figure 8:
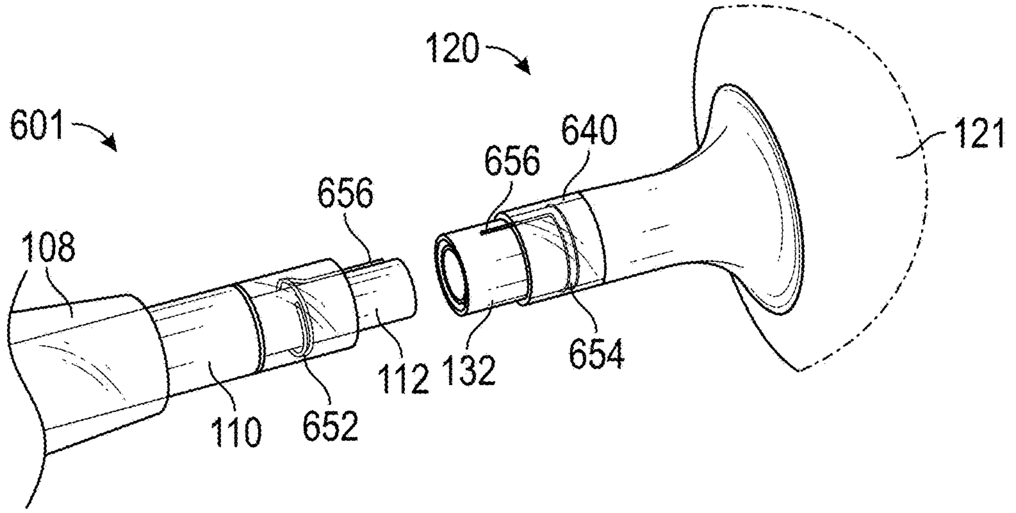
FIG. 8 is a partially transparent, perspective view of the distal portion shown in FIG. 6.

In some embodiments, the detachment element is not a portion of the manipulation shaft 110. For example, FIGS. 6-8 show another embodiment of a delivery system 601 having a detachment element 650 that comprises an additional member extending between the manipulation shaft 110 and a cured material 640 at the proximal end of the occlusive device 120. The delivery system 601 of FIGS. 6-8 can have generally the same features and components as the delivery system 101, and the cured material 640 can have the same features as the cured material 140 discussed above with reference to FIGS. 2A-2G except as noted in the following discussion. The detachment element 650 is configured to electrolytically corrode and break when current is applied to the manipulation shaft 110, as detailed below.

The delivery system 601 can include a power supply (not shown), and a proximal portion of the manipulation shaft 110 can be configured to be electrically coupled to the power supply. The manipulation shaft 110 (and thus the detachment zone 350) can comprise an electrolytically corrodible material. The power supply may also be coupled to a proximal portion of the handle 102 (FIG. 2A) or to the patient. A current can flow from the power supply through the manipulation shaft 110 to the detachment element 650, and to a return path via the delivery shaft 108, the injection shaft 112, and/or another structure extending near the detachment element 650. Alternatively, the current from the detachment element 650 may flow to the patient, and subsequently to ground or to the power supply. The power supply, for example, can be a direct current power supply, an alternating current power supply, or a power supply switchable between a direct current and an alternating current. In some embodiments, a positive terminal of a direct current power supply may be coupled to the proximal portion of the manipulation shaft 110 and a negative terminal of a direct current power supply may be coupled to the proximal portion of the handle 102. The power supply may provide a current through the treatment system to initiate an electrolytic process during use of the system 601 in a fluid medium such as a bloodstream, which may be used as an electrolyte.

The detachment element 650 can comprise a conductive, electrolytically corrodible filament having a first end 652 coupled to the manipulation shaft 110, a second end 654 embedded within the cured material 640, and a non-insulated severable portion 656 extending between the first and second ends 652, 654. In some embodiments, for example as shown in FIGS. 6-8, the detachment element 650 can be coupled to the manipulation shaft 110 by winding a portion of the detachment element 650 around an outer surface of the manipulation 110 shaft and placing a coupler 670 over the wind(s). The coupler 670 can be a crimped tube, a shrink tube, or other securing means. In some embodiments, the first end 652 of the detachment element 650 is secured by other suitable securing means, including via an adhesive, a thermoplastic resin, etc. In any case, the first end 652 of the detachment element 650 can be secured to the manipulation shaft 110 in such a way that the first end 652 is insulated by the coupler 670 or other securing means.

As shown in FIGS. 6-8, in some embodiments the manipulation shaft 110 has a narrowed distal portion 110*b* (relative to the remaining proximal portion 110*a* of the shaft 110), and the first end 652 of the detachment element 650 and the coupler 670 are positioned around the narrowed portion 110*b* such that the outer diameter of the narrowed distal portion 110*b*, the first end 652 of the detachment element 650, and the coupler 670 is no greater than the outer diameter of the proximal portion 110*a*. In some embodiments, the manipulation shaft 110 does not have a narrowed distal portion 110*b* and has a substantially constant outer diameter along its length.

The second end 654 of the detachment element 650 can be embedded within, and insulated by, the cured material 640. For example, the second end 654 of the detachment element 650 and optionally a distal portion of the severable portion 656 can be positioned on the proximal end region 132 of the inner layer 122 (either directly on the filament/cured material composite structure, or on a layer of cured material that has been deposited on the filament/cured material composite structure). The cured material 640 can extend radially over and around the second end 654 and over and around at least a distal portion of the severable portion 656. Thus, the cured material 640 can be disposed at least on the outer surfaces of the severable portion 656. In some embodiments, the composite structure also includes a cured material layer between the proximal end region 132 of the inner layer 122 and the radially inner surface of the detachment zone 650 and/or filament.

The manipulation shaft 110 can be insulated along its length but electrically coupled to the detachment element 650 so that current flowing through the manipulation shaft

110 flows through the detachment element 650. The detachment element 650 may be electrically insulated except along the severable portion 656 so that current applied through the manipulation shaft 110 selectively targets the severable portion 656 for electrolytic corrosion.

The detachment assembly shown in FIGS. 6-8 can be formed by any of the previously-described manufacturing processes.

According to some methods of use, the distal portion of the delivery system 601 can be positioned proximate an aneurysm and the occlusive device 120 can be pushed distally (via the manipulation shaft 110) beyond a distal end of the delivery shaft 108 and into the aneurysm. Release of the occlusive device 120 from the delivery shaft 108 allows the mesh 121 of the occlusive device 120 to self-expand. During and/or after deployment of the occlusive device 120, the embolic composition 202 (FIG. 2A) can be delivered into the aneurysm cavity through the injection shaft 112 extending through the cured material 140. To detach the occlusive device 120 from the delivery system 601, current can be applied to the manipulation shaft 110 to electrolytically corrode the non-insulated severable portion 656 of the detachment element 650. Prior to application of the current, the delivery shaft 108 can be withdrawn proximally beyond the detachment element 650 (if not already) to place the non-insulated portions of the severable portion 656 (e.g., proximal of the ledge 660) in contact with the bloodstream so that the blood can serve as an electrolyte for the electrolytic corrosion of the severable portion 656. After the severable portion 656 has been broken (as shown in FIG. 8), the manipulation shaft 110 and injection shaft 112 can be retracted and the occlusive device 120 may remain in position within the aneurysm.

Figure 9:
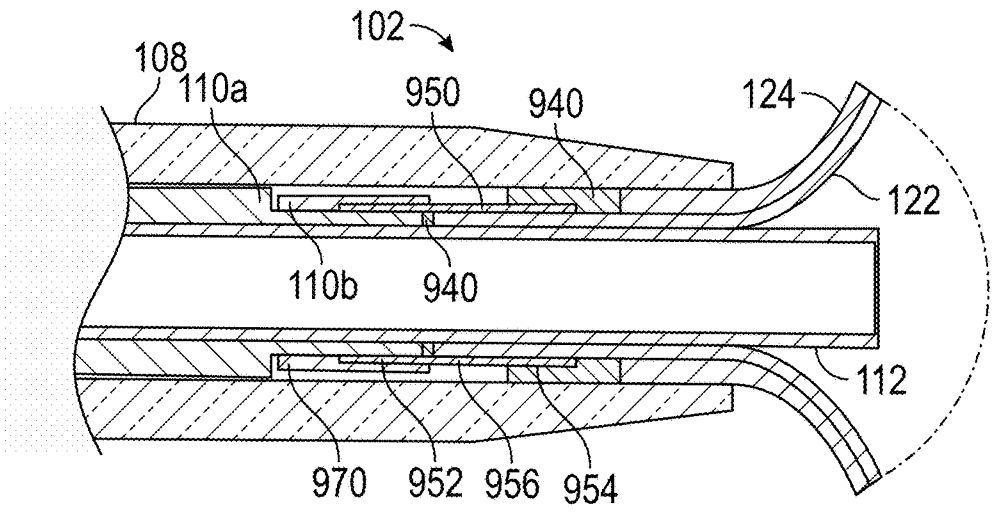
FIG. 9 is a cross-sectional view of a distal portion of a system for treating an aneurysm in accordance with embodiments of the present technology.
Figure 10:
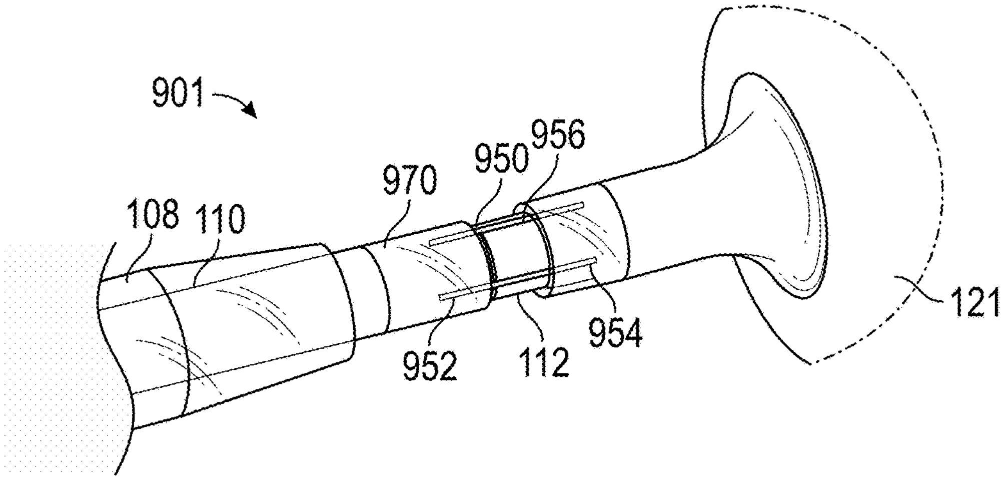
FIG. 10 is a partially transparent, perspective view of the distal portion shown in FIG. 9.
Figure 11:
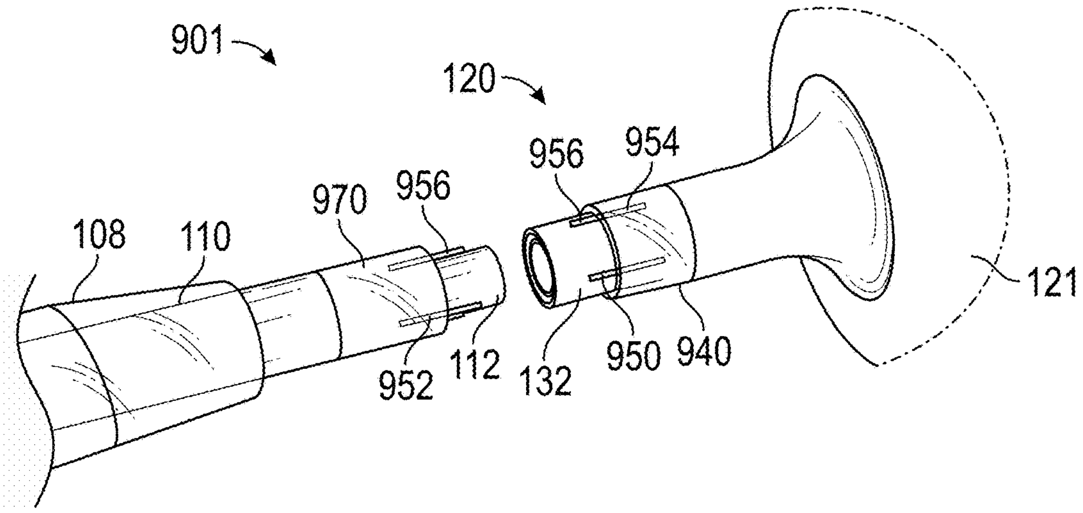
FIG. 11 is a partially transparent, perspective view of the distal portion shown in FIG. 9.

The detachment elements of the present technology can have shapes and configurations other than that shown in FIGS. 6-8. For example, as shown in FIGS. 9-11, the present technology can comprise a detachment element 901 can comprise a plurality of separate, conductive, electrolytically corrodible filaments 950 extending longitudinally between first ends 952 fixed at the manipulation shaft 110 (e.g., via a coupling element 970, such as a thermoplastic tube 970) and second ends 954 embedded in the cured material 940. Each of the filaments 950 can comprise a severable portion 956 between the first and second ends 952, 954. Unlike the first and second ends 952, 954, the severable portion 956 is non-insulated and configured to electrolytically corrode, as detailed above. The separate filaments 950 can be spaced apart around a circumference of the delivery system 901. While the filaments 950 are shown being generally linear in FIGS. 9-11, in other embodiments the filaments 950 can have one or more bends.

CONCLUSION

Although many of the embodiments are described above with respect to systems, devices, and methods for securing and delivering an occlusive device to a neurovascular aneurysm, the technology is applicable to other applications and/or other approaches, such as securement and delivery of other, non-braided and/or non-occlusive devices, treatment of vascular diseases other than aneurysms, and treatment of vascular disease in other parts of the vasculature. Moreover, other embodiments in addition to those described herein are within the scope of the technology. Additionally, several other embodiments of the technology can have different configurations, components, or procedures than those described herein. A person of ordinary skill in the art, therefore, will accordingly understand that the technology can have other embodiments with additional elements, or the technology can have other embodiments without several of the features shown and described above with reference to FIGS. 2A-11.

The descriptions of embodiments of the technology are not intended to be exhaustive or to limit the technology to the precise form disclosed above. Where the context permits, singular or plural terms may also include the plural or singular term, respectively. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. The various embodiments described herein may also be combined to provide further embodiments.

As used herein, the terms "generally," "substantially," "about," and similar terms are used as terms of approximation and not as terms of degree, and are intended to account for the inherent variations in measured or calculated values that would be recognized by those of ordinary skill in the art.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. A treatment system, comprising:

a manipulation shaft having a proximal portion and a distal portion;

an occlusive element coupled to the distal portion of the manipulation shaft, the occlusive element comprising a proximal end, a distal end, and a plurality of filaments secured to one another at the proximal end by a cured material and without a band or other mechanical restraint, wherein the cured material defines a channel extending therethrough; and a detachment element comprising a first end carried by the distal portion of the manipulation shaft and a second end embedded within the cured material at the proximal end of the occlusive element such that the detachment element couples the manipulation shaft to the occlusive element, wherein the detachment element is configured so that application of current through the detachment element causes the detachment element to selectively break between the manipulation shaft and the cured material, thereby decoupling the occlusive element from the manipulation shaft;

wherein the plurality of filaments further comprise an inner layer of braided filaments and an outer layer of braided filaments, each layer comprising proximal end regions, and wherein the proximal end region of the inner layer extends proximally beyond the proximal end region of the outer layer.

2. The treatment system of claim 1, wherein the channel is configured to receive an injection shaft therein.

3. The treatment system of claim 1, wherein the channel is configured to receive an embolic composition therethrough.

4. The treatment system of claim 1, wherein the cured material comprises a first region with a first diameter and a second region with a second diameter greater than the first diameter, the second region being distal of the first region along a longitudinal axis of the occlusive element.

5. The treatment system of claim 4, wherein the second end of the detachment element is embedded within the first region of the cured material.

6. The treatment system of claim 1, wherein:

the cured material comprises a first region with a first diameter and a second region with a second diameter greater than the first diameter, the second region being distal of the first region along a longitudinal axis of the occlusive element, the first region of the cured material surrounds and couples a portion of the proximal end region of the inner layer that extends proximally beyond the outer layer, and the second region of the cured material surrounds and secures the proximal end regions of both the inner and outer layers.

7. The treatment system of claim 1, wherein the cured material extends radially between the plurality of filaments at the proximal end of the occlusive element.

8. The treatment system of claim 1, wherein the detachment element comprises a region of a tubular sidewall having a plurality of longitudinally extending fingers defining a plurality of windows, each window positioned between circumferentially adjacent fingers, and wherein each window comprises a cut-out region in the tubular sidewall.

9. An occlusive device, comprising:

a proximal region configured to receive an injection shaft therethrough and a distal region configured to be positioned within an aneurysm;

a first layer of braided filaments secured to one another at the proximal region by a cured material and without a band or other mechanical restraint; and a second layer of braided filaments secured to one another at the proximal region by the cured material and without a band or other mechanical restraint, wherein the first layer of braided filaments is radially surrounded by the second layer of braided filaments, and a proximal end of the first layer is disposed proximal of a proximal end of the second layer along a longitudinal axis of the occlusive device.

10. The occlusive device of claim 9, wherein the injection shaft is configured to receive an embolic composition therethrough.

11. The occlusive device of claim 9, wherein the cured material comprise a first region with a first diameter and a second region with a second diameter greater than the first diameter, the second region being distal of the first region along the longitudinal axis of the occlusive device.

12. The occlusive device of claim 9, further comprising a detachment element having a first end and a second end, wherein the second end is embedded within the cured material and configured to selectively break along a non-insulated region following application of an electric current.

13. The occlusive device of claim 11, wherein:

the first region surrounds and couples a portion of the proximal end of the first layer that extends proximally beyond the second layer, and the second region surrounds and secures the proximal ends of both the first and second layers.

14. The occlusive device of claim 9, wherein the cured material extends radially between the braided filaments of the first and second layers at the proximal end of the occlusive device.

15. The occlusive device of claim 12, wherein the detachment element comprises a region of a tubular sidewall having a plurality of longitudinally extending fingers defining a plurality of windows, each window positioned between circumferentially adjacent fingers, and wherein each window comprises a cut-out region in the tubular sidewall.

16. The occlusive device of claim 9, wherein the cured material is configured to hold the first layer and the second layer together.

17. The occlusive device of claim 9, wherein longitudinal spacing between the proximal end of the first layer and the proximal end of the second layer creates a step, and the cured material is configured to conform to a shape of the step.

* * * * *